United States Patent

Schoenen et al.

Patent Number: 5,228,343
Date of Patent: Jul. 20, 1993

[54] ULTRASOUND TESTING DEVICE FOR THE NON-DESTRUCTIVE TESTING OF WORKPIECES

[75] Inventors: Manfried Schoenen, Mettmann; Harri Haacke, Ratingen-Vokarday; Hans-Jürgen Bäthmann, Moers; Bernhard Karbach, Erfstadt-Friesheim; Gerd Kauth, Cologne; Reinhard Prause, Augustin; Ottokar Patzke, Erfstadt-Liblar, all of Fed. Rep. of Germany

[73] Assignees: Mannesmann AG, Dusseldorf; Krautkramer GmbH & Co., Hurth, both of Fed. Rep. of Germany

[21] Appl. No.: 747,786

[22] Filed: Aug. 19, 1991

[30] Foreign Application Priority Data

Aug. 17, 1990 [DE] Fed. Rep. of Germany ....... 4026458

[51] Int. Cl.⁵ ............................................ G01N 29/28
[52] U.S. Cl. ...................................................... 73/644
[58] Field of Search ................ 73/625, 628, 632, 641, 73/644

[56] References Cited

U.S. PATENT DOCUMENTS

| | | | |
|---|---|---|---|
| 3,712,119 | 1/1973 | Cross et al. | 73/625 |
| 3,927,662 | 12/1975 | Ziedonis | 73/641 |
| 3,978,714 | 9/1976 | Shraiber et al. | 73/625 |
| 4,305,297 | 12/1981 | Ries et al. | 73/628 |
| 4,526,038 | 7/1985 | Box et al. | 73/644 |

FOREIGN PATENT DOCUMENTS 2751810  11/1977  Fed. Rep. of Germany .

Primary Examiner—Hezron E. Williams
Assistant Examiner—Rose M. Finley
Attorney, Agent, or Firm—Cohen, Pontani, Lieberman, Pavane

[57] ABSTRACT

An ultrasound testing device for the non-destructive testing of a workpiece wherein at least three testing heads are disposed on a testing head carrier, and the testing heads emit sound waves which converge at one or more intersections in an area of the workpiece so as to detect defects and determine the wall thickness. Operationally, the number of intersections is one less than the number of testing heads, and the separation between the sound waves is chosen so as to avoid the disturbances associated with utilization of oppositely situated testing heads. In addition, the device uses a flow medium to couple the testing heads to the surface of the workpiece.

11 Claims, 6 Drawing Sheets

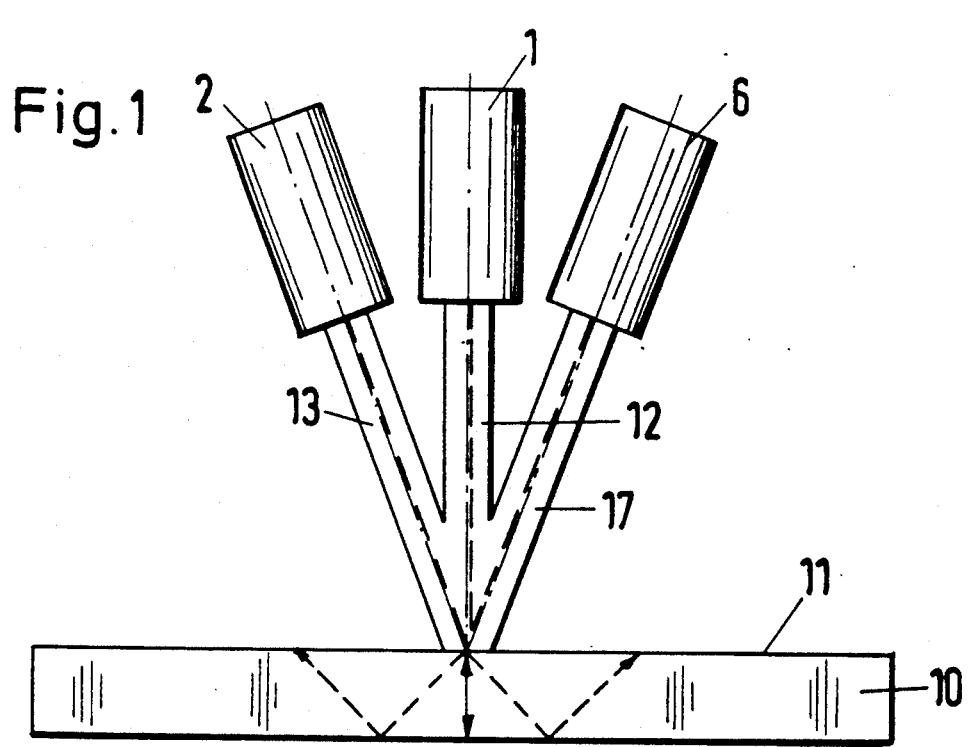
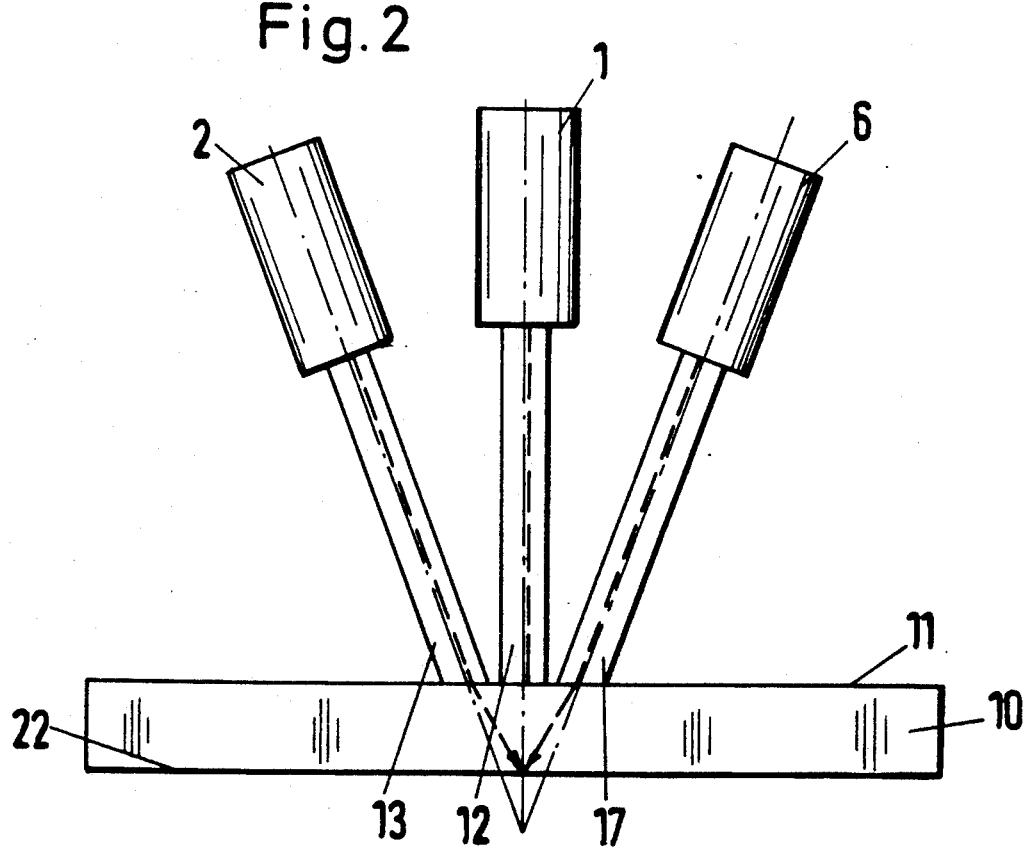

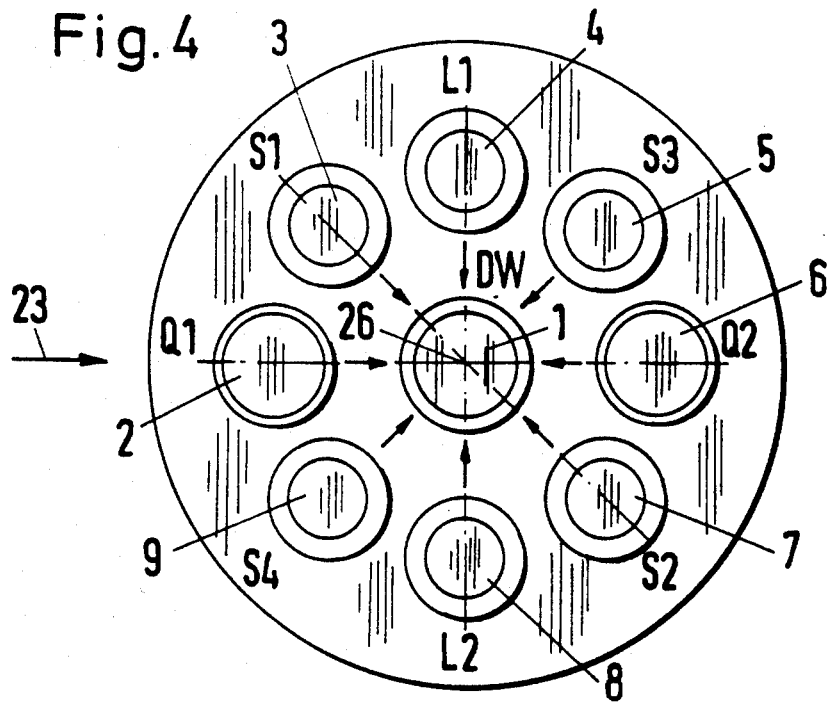
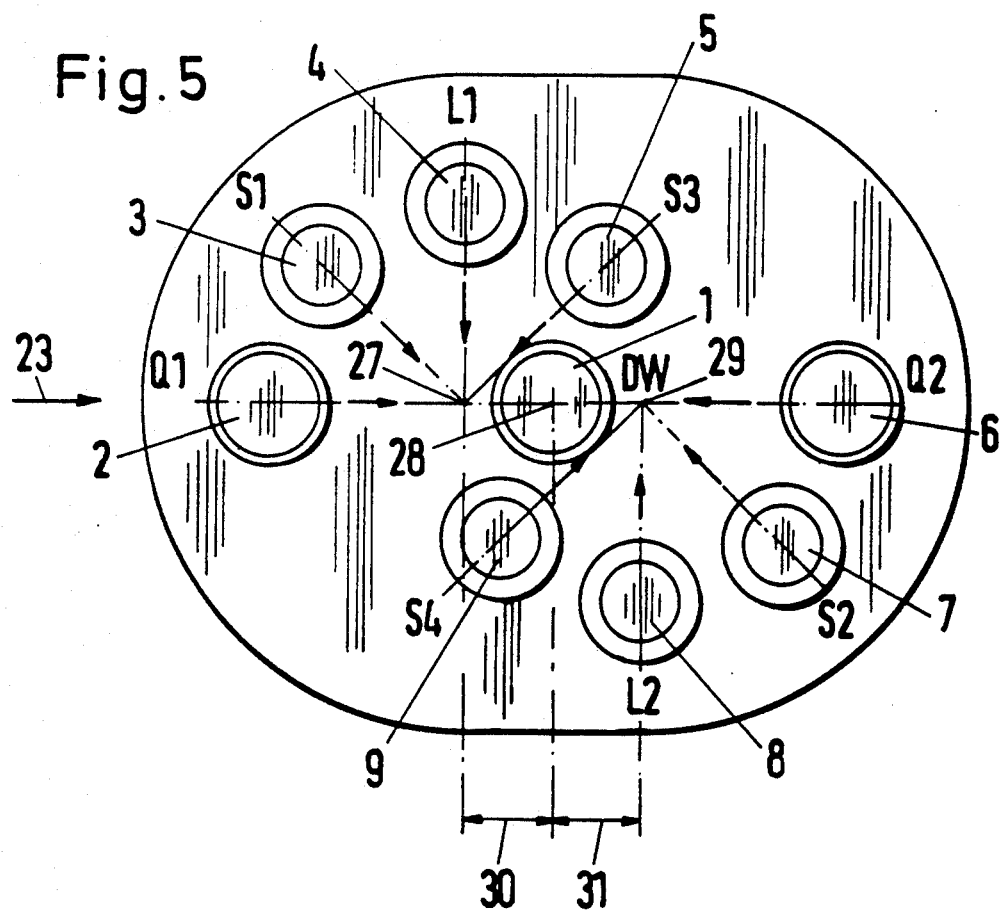

ULTRASOUND TESTING DEVICE FOR THE NON-DESTRUCTIVE TESTING OF WORKPIECES

BACKGROUND OF THE INVENTION

The state of the art discloses an ultrasound testing device consisting of a testing-head carrier having entry drill holes for coupling water and an exchangeable chamber attached thereto for containing (receiving) the coupling medium as well as a guiding mechanism connected to the device. In the center of the testing-head carrier, a testing head is provided so as to emit vertical sound waves in order to check wall thickness and lamination or double draw which can occur during the manufacture of a metal, particularly the rolling of steel. In addition, four testing heads are situated in a circle, each staggered 90 degrees, emitting slanted waves in order to detect defects. Two testing heads situated opposite one another form a pair in order to perform the same type of defect testing, i.e., one for longitudinal and one for transversal defect testing. The axes of the sound waves from the five testing heads focus on the surface of the test piece at a common testing spot. In order to form an aqueous path for the waves, an exchangeable chamber with a central water containing channel is positioned at the testing-head carrier. In order to eliminate the disturbing sound reflection generated at the walls of the channel, the channel wall is provided with a 90 degree corrugation showing a slope. In order to position the ultrasound testing device on top of the test piece, the device is connected with a guiding mechanism displaying protective bottom pads shaped in conformance with the contour of the test piece and being in contact with the test surface during testing. The disadvantage of the above described device is readily apparent in the unsatisfactory performance due to the low pulse sequence frequency and the device's inability to operate disturbance-free during the conducting of the water.

From German Patent Application OS 27 51 810, an ultrasound testing device for non-destructive testing of welding seams is known, whereby a total of six testing heads are placed in a testing spindle, and the sound waves intersect at one point. The sound-conveying coupling medium is achieved by feeding water to the contact plane. A drawback of this arrangement is that the coupling medium is fed in an uncontrolled manner to the testing device and that thereby the coupling control expense is very high. Moreover, due to cyclic prompting of the individual testing heads, the performance of the device is very low, since it is necessary to wait for the echo of the input pulse before the next pulse can be generated. A further significant disadvantage is the fact that the testing heads are mounted in individual holders that change their positions relative to each other when tolerances of the testing piece or tolerances in transport and guiding occur.

SUMMARY OF THE INVENTION

It is an object of the invention to provide an improved ultrasound testing device with which tests resulting in high test performances and non-susceptibility to disturbances is achieved and which is readily adaptable to various testing tasks and shapes of the test piece.

This object is achieved by providing an ultrasound testing device for the non-destructive testing of a workpiece wherein at least three testing heads are disposed on a testing head carrier, and said testing heads emit sound waves which converge at one or more intersections in an area of the workpiece so as to detect defects and determine the wall thickness. Operationally, the number of intersections is one less than the number of testing heads and the separation between said sound waves is chosen so as to avoid the disturbances associated with utilization of oppositely situated testing heads. In addition, the device uses a flow medium to couple the testing heads to the surface of the work piece.

It is essential to the invention that the central channel of the chamber conducting the flow medium is split into separate channels, whereby the number of channels corresponds to the number of the provided testing heads and the axes of the channels are in alignment with the respective sound wave axis. By providing for each testing head a separate path for conducting the flow medium in the shape of a channel, which extends over a certain length of the chamber, the formation of straying sound pulses is substantially suppressed. Consequently, the useful signal/noise ratio is increased significantly and the testing is performed with a higher pulse sequence frequency. Moreover, through the use of separate paths, the coupling conditions improve, since the coupling medium is better guided. A further significant aspect of the invention follows from the fact that, when testing, for example, pipes or solid bars in the three o'clock or nine o'clock position, and in particular the 12 o'clock position, care is taken that air bubbles possibly gathering in remote areas will be flushed away through the movement of the coupling medium. Moreover, the testing head carriers and the chambers are arranged relative to each other in such a manner that in the area enclosing all testing heads and inlet openings for the channels, an outwardly sealed slit conducting the flow medium is formed. The outlet openings of the symmetrically arranged entry channels lead to the peripheral-zone of this water-conducting slit.

It is thus ensured that the entire slit volume is completely filled up with the coupling medium and that the pressure as well as the circulation are uniform. In order to ensure that no accumulation of air bubbles occur at a remote location, a ventilation duct in the testing head carrier is also provided at the furthest distance from the end surface of the chamber and that it is in connection with the slit conducting the flow medium. In order for the testing device to be universally applicable for different positions, several vents in the testing head carrier are provided that may be optionally open or closed. Furthermore, in order that no disturbing accumulation of air-bubbles in the area of the testing heads themselves occur, the testing heads are attached in such a manner in the drill holes of the testing head carrier that the end surfaces of the testing head is flush at least with the drill-hole exit surface, or even better, juts out from it.

The number and arrangement of the testing heads in the testing head carrier can be freely selected within certain limits. One limit is established by the fact that for reasons of easy handling, it is attempted to make the testing head carrier as small as possible, so that it may be used for example as a rotation head for testing pipes or rods. Other limits are governed by the geometrical conditions of the selected vibrator size and the physical characteristics, such as frequency and length of the near environment.

In a first embodiment, at least two testing heads are provided. In principle, this embodiment corresponds to two separately functioning testing heads, with only one difference, i.e., that the sound waves intersect at a point within the area of the workpiece. This way all information is obtained from one and the same spot and no further efforts of an electronic nature are needed to combine the signals of the individual testing heads with each other in an manner faithfully corresponding to the spot.

In order to satisfy the international testing requirements, it is necessary to test in the opposite incident direction to ensure that a remotely situated defect with respect to its reflection surface toward the original incident sound direction can be traced. This can be accomplished by turning the already described testing device 180 degrees and repeating the test. However, due to the time for testing and the material flow required, it is desirable to avoid a second throughput of the workpiece. Consequently, it is suggested, as a further development, to provide for an additional testing head carrier adjacent to the first mentioned testing head carrier. In this manner, the incident sound direction of the provided testing heads would be opposite to that of the first testing head carrier. With such an arrangement, all known test requirements could be satisfied, thus making parallel operation of all testing heads possible. However, one disadvantage is the added effort involved. The device would be relatively large, since two separate testing head carriers must be exactly lined up and maintained, while the two forming testing spots are located at a far distance from each other, which in turn necessitates electronic correlation.

As a result of the above, it is preferable to arrange a total of nine testing heads in a testing head carrier. With the exception of the centrally positioned testing head, the other 8 testing heads are staggered 45 degrees in a circle, or in a star-shaped arrangement, around the central testing head. With this arrangement, the testing heads are split into a pair of testing heads for the longitudinal and another pair for the transversal defect testing, while two testing head pairs are used for slanting defect testing. The centrally positioned testing head is preferably used for wall thickness and lamination/double draw testing. In addition, it concurrently serves as a coupling control. With this configuration, and for all testing head pairs, the two testing heads work together and are positioned exactly opposite from one another. Furthermore, it is an advantage, if there is only one common test spot for all testing heads, so as to obviate the need for a correlation between the received signal and its corresponding test spot. The common test spot may be situated on the external surface of the test piece or at the back wall thereof. The first mentioned variant has the advantage that the testing is independent within a wide range of test piece measurements. This range, however, is limited due to the refraction characteristics of the ultra sound in the workpiece, since at a certain degree of thickness, the sound waves no longer reach the back wall. As a result, the angle of the sound waves must be changed in order to test workpieces with thicker walls. As an alternative, it is possible to place the common testing spot on the back wall. However, this has the disadvantage that for each thickness, a new adjustment becomes necessary. As a result, the setting of the test spot will only be used, when testing large lots having identical measurements. The advantage of the above mentioned test spot setting is apparent, in its ability to detect with high probability remotely located inner defects. For certain test jobs, it may be practical to arrange the common test spot within the extension of the workpiece thickness, i.e., between the external surface and the back wall.

The above described circular or star-shaped arrangement of the testing heads, however, has the drawback of forming testing-head pairs situated opposite each other. Under the circumstances, sound waves are unavoidably directed towards opposed testing heads so as to mutually influence each other's pulses (i.e. one testing head may reach the opposite testing head as a result of the reflection at the surface of the test piece). It is therefore suggested in the alternative that at least three testing heads be used whereas one testing head pair is staggered. Moreover, the general condition should apply that the number of testing heads should always be greater than the number of the occurring testing spots. The formation of only one single common testing spot is abandoned with this configuration and at least two testing spots are needed, and whereby the distance between both testing spots is made as small as possible. The necessary distance between pairs of testing heads situated across from each other depends upon the size of the vibrator, the frequency, and the sound field funnel, and said distance has the size of, e.g, (N−1) times the diameter of the testing heads, whereby n is the number of the formed testing spots. The myriad of possible arrangements of the testing heads will not be discussed in detail. However, it is significant to note that they represent a compromise between the formation of only one testing spot and the mutual non-influencing of testing heads working together as pairs. By arranging the testing head in pairs which are staggered with respect to each other, parallel operation becomes possible so as to permit the use of a relatively high pulse sequence frequency. With the formation of only one common testing spot, only one cyclic transmission operation is possible in order to eliminate the disturbing influence of the sound waves directed toward each other, which results in a corresponding reduction in the pulse sequence frequency.

In order to increase the quick and simple adaptability of the device to various testing jobs, it is suggested that the chamber be designed as a bushing, in which an exchangeable insert is provided having channels for conducting the flow medium. With regard to the cross section and the tilt of the channels, the above arrangement permits the production of various ready made inserts that are adaptable to most testing jobs. An exact adjustment of the testing heads is made easier by the fact that they are adjustably attached in the testing head carrier in the axial direction. Moreover, it is possible to offset the previously determined angle of squint of the testing head by using and turning eccentric bushings that can be inserted in the testing head carrier. In order to optimize the distribution of the flow medium, a total of four entry drill holes are provided which are symmetrically distributed in the testing head carrier. If the testing head carriers are used in accordance with the invention to test pipes or the like, the device should be arranged on gimbals so that it may adapt itself to the contours of the workpiece. Furthermore, the prismatically shaped protective bottom pads transversal to the axis of the test piece are adjustably connected with the test device. The adaptation of the guiding mechanism to varying diameters of the pipe to be tested is thereby simplified. With a stationary testing head carrier, the pipe would move in a helical fashion, in order to insure a complete scanning. In the alternative, the pipe may move without turning around its longitudinal axis, if instead the testing head carrier rotates around the pipe. As yet another alternative, the testing head carrier may be transported along a pipe while the pipe remains in one spot and turns around along its longitudinal axis. In order to further increase the test performance, it is further suggested that four testing head carriers staggered 90 degrees or behind each other in a frame, be used so that it may be tilted in and out of the test line for adjustment and reconstruction.

BRIEF DESCRIPTION OF THE DRAWINGS

The device according to the invention is described in the drawings in which:

FIG. 1 is a schematic illustration of the common testing spot - external surface of the workpiece;

FIG. 2 is a schematic illustration of the common testing spot - back wall of the workpiece;

FIG. 4 is a top view of the schematic illustration of a circular testing head carrier incorporating 9 testing heads;

FIG. 5 is a top view of the schematic illustration of an oval testing head carrier incorporating 9 testing heads;

DETAILED DESCRIPTION OF THE PRESENTLY PREFERRED EMBODIMENTS

Figure 3:
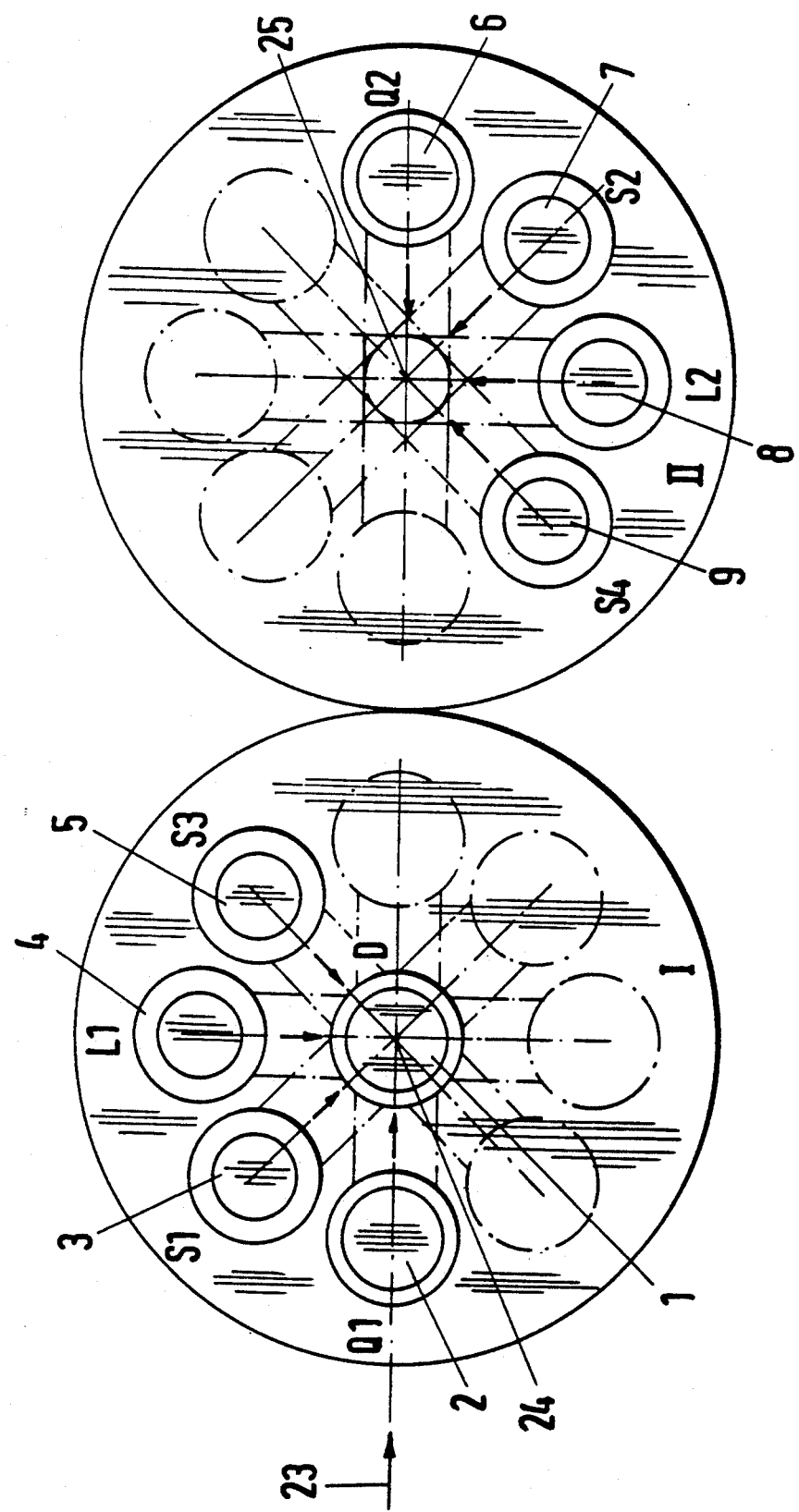
FIG. 3 is a top view of the schematic arrangement of two testing head carriers I, II each with a common testing spot and the corresponding sound absorptive drill holes positioned opposite one another.

FIG. 1 in a schematic illustration shows an arrangement according to the invention with three testing heads 1, 2, 6 lying in one plane in which the sound waves (dashed lines) are directed at the workpiece 10 to be tested in such a manner that the common testing spot is formed at the external surface 11 of the workpiece 10. Coupling occurs via a flow medium, e.g., water which is led through separately arranged channels 12, 13, 17 schematically illustrated here. The axes (the dash-dotted lines) of channels 12, 13, 17 are in alignment with the sound waves and intersect at a point directly on the surface 11 of the workpiece 10. In FIG. 2, an arrangement similar to that of FIG. 1 is shown, the only difference being that the common testing spot is formed on the back wall 22 of the workpiece 10. When testing a pipe, this would correspond to the inner wall. With this configuration, the sound waves (dashed lines) are in alignment with the axes (dash-dotted lines) of channels 12, 13, 17. However, the imaginary point of intersection of the axes lies outside of the workpiece 10, while the axes of the sound waves intersect at a point on the back wall 22. Between these two extreme positions according to FIGS. 1 and 2, the formation of a common testing spot somewhere inside the wall of the workpiece 10 is also conceivable.

In FIG. 3, the arrangement of two separate testing head carriers I, II is schematically illustrated. With regard to testing heads 1 to 9, and their respective opposite sound absorptive drill holes, the following abbreviations are used in FIGS. 3, 4, and 5.

DW = Double Draw/ Lamination defect testing and wall thickness testing

Q1, Q2 = transverse defect testing

L1, L2 = longitudinal defect testing

S1-S4 = slanting defect testing

The thickly drawn arrow 23 is intended to indicate the entry direction of the workpiece, which is not shown here. In a first embodiment of the present invention, the testing head carrier has a total of three testing heads 1, 2, 4 or even as little as two testing heads 2, 4 and respective sound-absorptive drill holes. The workpiece could then be tested in only one incident sound direction, for example, for longitudinal and transversal defects and by adding the centrally positioned testing head 1 for wall thickness and lamination/double draw defects. Moreover, testing head 1 could assume the function of the coupling control. The effect of the additionally arranged opposite sound absorptive drill holes is explained in more detail with regard to FIG. 8. As an expanded embodiment, at least one more testing head could be added for the slanting defect testing. If two additional testing heads 3 and 5 were added for slanting-defect testing, the arrangement would then correspond to the testing head carrier shown in FIG. 3. It is characteristic of testing head carrier I for the sound waves (here symbolized by the arrows pointing away from the testing heads) to intersect in only one point 24 (the testing spot and with the exception of the centrally arranged testing head 1 for lamination and wall-thickness testing, the other four testing heads 2 to 5 to be arranged in a circle and at a distance from the central testing head 1. Since the sound waves of testing heads 2 to 5 with their slanted incident sounding do not mutually influence each other and since internal disturbance is prevented by the sound absorptive channel situated opposite each of the testing heads 2, 3, 4, and 5, parallel operation is made possible. However, the use of such a testing head carrier I is only possible if the test specifications to be observed do not oppose it and the location and the type of the most frequently occurring defect is known with a certain degree of accuracy.

Internationally known test specifications prescribe a incident sound direction in two opposing directions for the reliable detection of defects in a workpiece. This requirement can be satisfied by turning the first-mentioned testing head carrier I about 180 degrees and by letting the workpiece traverse this testing head carrier I one more time. This problem can be solved, however, somewhat more elegantly by arranging an additional testing head carrier II displaying an arrangement comparable to that of testing heads 6-9, in the immediate vicinity of the first testing head carrier I. The difference with regard to the first testing head carrier I is that the incident sound directions at the testing heads are opposite each other. The sound waves of testing heads 6-9 of the second testing head carrier II are arranged in beams similar to those of the first testing head carrier I, so that a common point of intersection 25 (testing spot) is formed in which the distance to the first-mentioned point of intersection 24 of the first testing head carrier I is equal to at least the length of one diameter of the testing head carrier.

It is an advantage of this embodiment that the testing heads 1-5 and 6-9 of each of the testing head carriers I, II can be operated in parallel fashion, since the sound waves do not disturb each other. A drawback however is the amount of engineering required in order to support the two testing head carriers I, II and the effort to adjust them on a common axis. The two points of intersection 24, 25 of the sound waves are a disadvantage insofar as it makes necessary a corresponding correlation with respect t the test spot of the received signals.

Due to these drawbacks, an embodiment as shown in FIG. 4 is preferred, in which a total of 9 testing heads 1-9 are arranged in one single testing head carrier. The sound waves of testing heads 1-9 are directed such that only one single point of intersection 26 (test spot) is formed, which corresponds to the illustrations as shown in FIGS. 1 and 2, and which may be optionally located on the external surface 11 or on the back wall 22 of the workpiece to be tested. With the shown arrangement, pairs of testing heads form that lie opposite each other and the sound waves are directed in opposite directions. For instance, testing heads 4, 8 form a testing head pair for longitudinal defect testing, whereby as seen from the direction of entry 23, testing head 8 situated on the right produces incident sounds counterclockwise and the left positioned testing head 4 clockwise. An advantage of this arrangement is the possibility of enabling a compact construction of the testing head carrier so that only a small space is required for the holder frame and the guidance. In addition, in this compact form, it may be used as a rotational testing head as well. Only one common point of intersection 26 (testing spot) forms, so that all information originates from one and the same place and no correlation with respect to the exact spot is required. A disadvantage, however, is the disturbing influence of the sound waves from the testing heads located opposite each other which cannot be avoided, so that parallel operation of all testing heads is impossible under normal situations. This problem can be solved by using the multiplex method, whereby, in terms of test performance, the desired high pulse sequence frequency must be reduced correspondingly.

An alternate embodiment is illustrated in FIG. 5. For this testing head carrier nine testing heads 1-9 are arranged such that a total of three points of intersecticns 27, 28, 29 (testing spots) are formed, separated by a distance 30, 31 which corresponds to one testing head diameter. It is attempted to keep this distance 30, 31 as short as possible without it leading to a disturbing influence of the sound waves caused by the staggered arrangement of the testing heads, e.g., 5, 9. The testing head carrier is then no longer circular, but oval and therefore requires more space than the testing head carrier depicted in FIG. 4. The advantage of this arrangement is that parallel operation of all testing heads 1-9 becomes possible and that correspondingly the pulse sequence frequency may be very high, which enhances the test performance. The drifting apart of the testing heads and the formation of three separate points of intersection 27, 28, 29 (testing spots) is acceptable since the amount of correlation required is low as compared to the arrangement utilizing two separate testing head carriers I, II and as shown in FIG. 3.

With reference to the illustration of the testing head carriers shown in FIGS. 3, 4, 5, it should be emphatically pointed out that the chosen arrangement of the testing heads and their assignment to a certain test function are only meant as examples. A plurality of other combinations are possible without exceeding the extent of the protection and scope of the invention.

Figure 6:
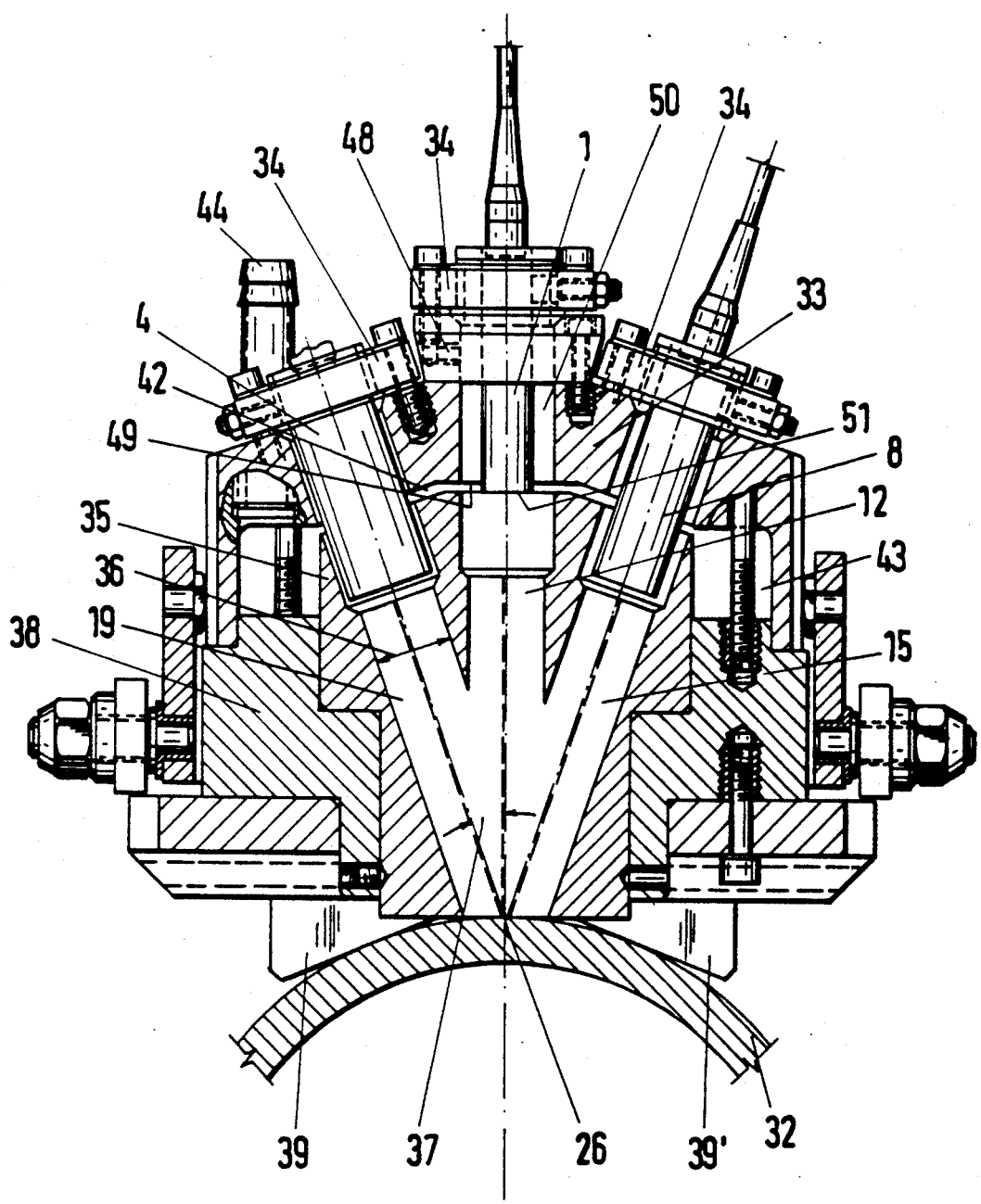
FIG. 6 is a cross section of an embodiment of a test device according to the arrangement illustrated in FIG. 4.
Figure 7:
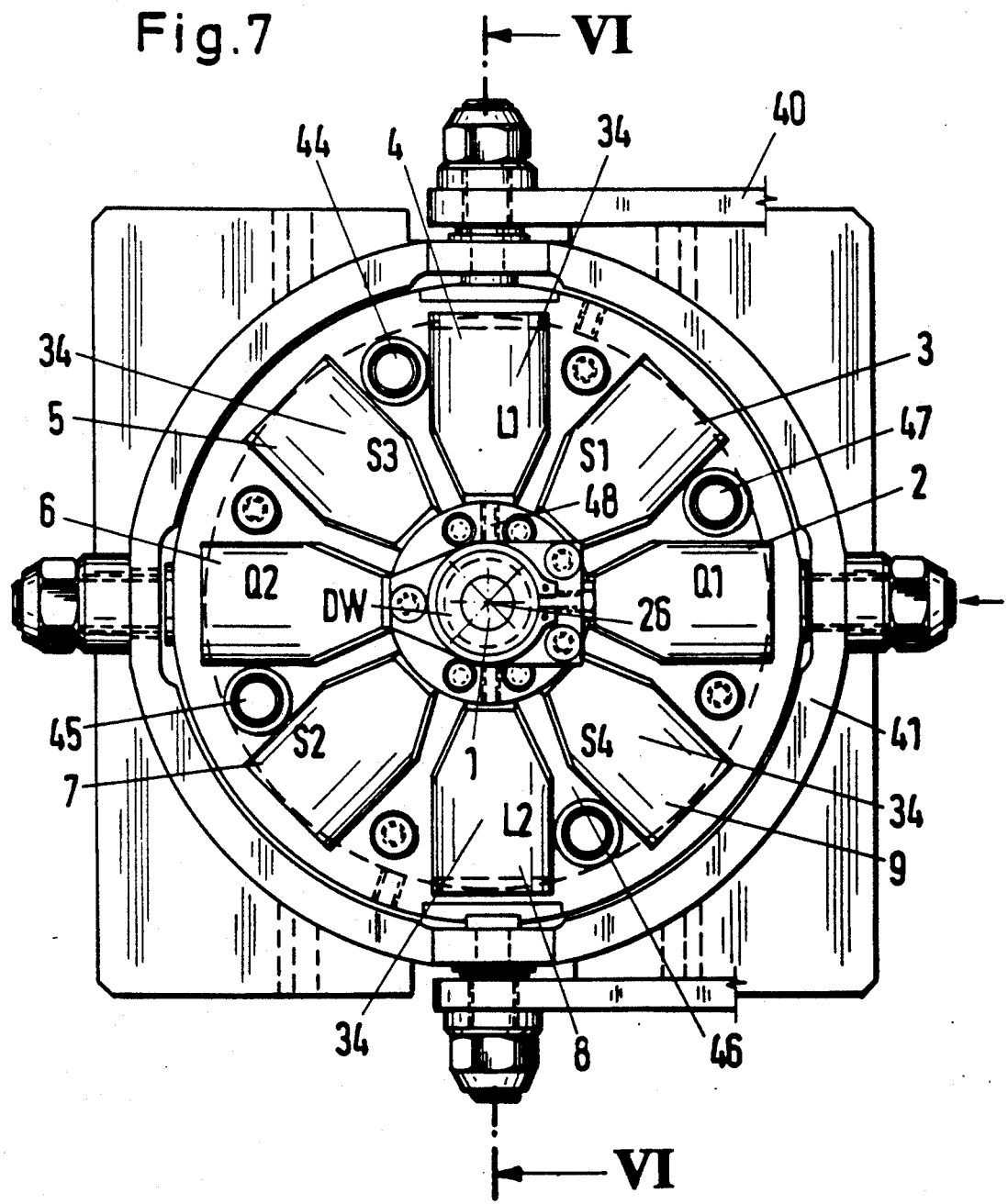
FIG. 7 is a top view of the testing head carrier.

The test device according to the invention and schematically illustrated in FIG. 4 is shown in cross-section in FIG. 6 and as a top view in FIG. 7. As an example, a pipe 32 in the 12 o'clock position is tested although testing at the 3, 6, or 9 o'clock position can be simulated by correspondingly turning the figure. The test device consists of a testing head carrier 33 in which a total of 9 testing heads 1-9 are provided in the schematically illustrated arrangement according to FIG. 4. The testing heads 1-9 are attached by means of sheet-metal holders 34 to the testing head carrier 33 in such a manner that they may be locked in position with axially different depths. Moreover, the axial directions of testing heads 1-9 may be adjusted within certain limits, so that the axes of the sound waves (here indicated by dashed lines) align exactly with the axes of channels 12-20 (here indicated by dash-dotted lines). According to the present invention each of the testing heads 1-9 is assigned a channel 12-20 for conducting the flow medium, and whereby in this embodiment, channels 12-20 consist of cylindrical bore holes. In order to adapt the test device to various testing tasks, channels 12-20 are arranged in an exchangeable insert 35, so that the cross-sectional form, the diameter 36 and the angularity of the axis 37, which in this case represents 19 degrees, can be varied. Insert 35 is held by a bushing 38, which is solidly connected to the testing head carrier 33. At the underside of bushing 38, the guiding mechanism is positioned, which in the case of the pipe testing, shows two adjustable bases 39, 39' in the shape of prisms. With regard to an exact adjustment of the test device, when testing workpieces with rounded surfaces, the testing head carrier 33 including the insert 35 attached thereto and the bushing 38 is suspended on gimbals in a frame 40, 41.

For a disturbance-free guidance of the flow medium, the insert 35 of the testing head carrier 33 is arranged in such a manner, that a slit forms in the connection area. In this embodiment, this slit 42 is dome-shaped and extends over all inlet openings of channels 12-20. In the area of the peripheral zone, the slit 42 expands to form a ring-shaped space 43 into which entry channels 44-47 lead for the introduction of flow medium. At the highest point of the slit 42, or generally at the furthest distance from the workpiece surface, a vent 48 is provided. In order to make the testing device universally useable for all circular positions, further ventilation drill holes (not shown here) have been provided that may optionally be either open or closed. Furthermore, in order to minimize the accumulation of air bubbles in the area of the testing heads 1-9, the testing heads 1-9 are fastened in such a manner in the testing head carrier 33 that the end surface of the testing heads 1-9, here for example the number 51 of the centrally arranged testing head 1, extends beyond the exit surface 49 of the drill hole 50, or at least terminates in alignment with it. For both testing heads 4, 8 depicted here, the end surface juts widely into the respective channels 15, 19 of the insert 35.

Figure 8:
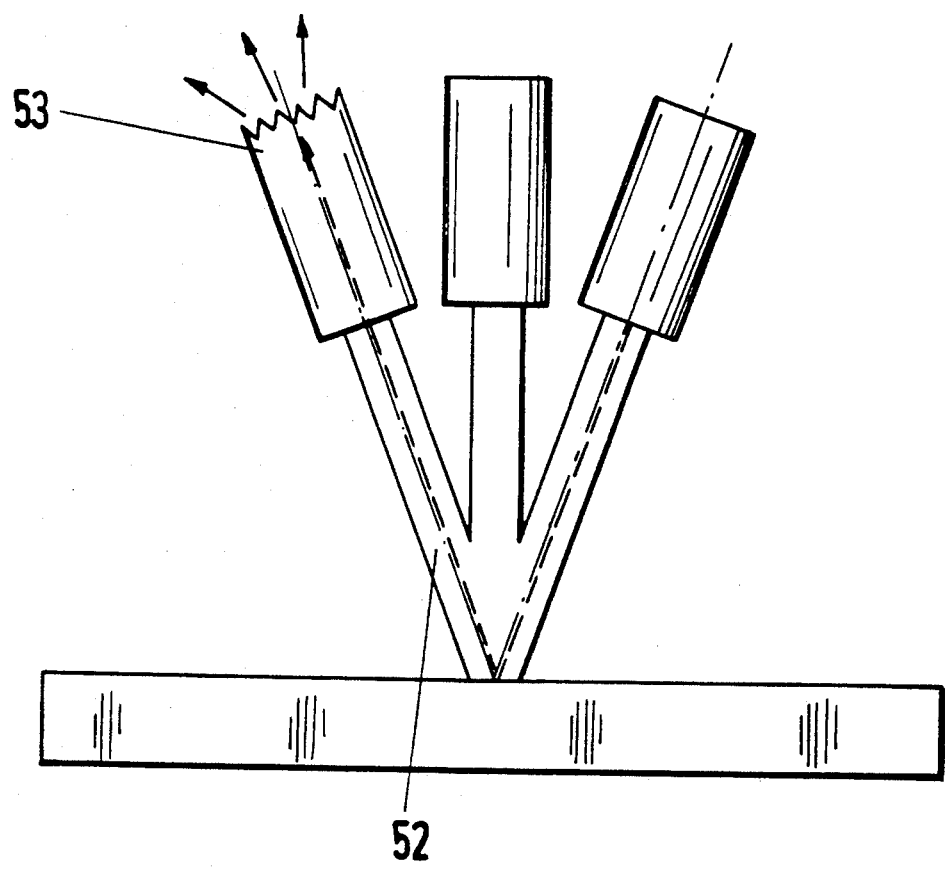
FIG. 8 is a schematic illustration of an embodiment designed to prevent disturbing reflections.

FIG. 8 shows a schematic illustration of the arrangement of a sound absorptive channel 52 incorporating a dampening material 53. This arrangement has the effect that the reflections possibly leading to disturbance indications with an embodiment having an asymmetric arrangement of the testing heads can be avoided. The reflections always appear when a discontinuity is formed at the exit in the replaceable insert 35 through unpaired drilled channels. This applies both for the embodiment according to FIG. 3 and for the embodiment according to FIG. 5.

It should be understood that the preferred embodiments and examples described are for illustrative purposes only and are not to be construed as limiting the scope of the present invention which is properly delineated only in the appended claims.

What is claimed is:

1. An ultrasound apparatus for the non-destructive testing of a workpiece by the pulse-echo method, comprising:
   (a) a testing head carrier having a chamber for receiving and guiding a flow medium, and a flow medium outlet contacting said workpiece;
   (b) a number of at least three testing heads disposed on said carrier in liquid communication with said flow medium and comprising means for generating and emitting sound waves along axes which converge at a number of at least two points of intersection, the number of said points of intersection being one less than the number of said testing heads;
   (c) said chamber further comprising a number of at least three channels, each of said channels being associated with one of said testing heads so that the number of said channels equals the number of said testing heads, said channels providing a path of predetermined length for receiving said flow medium and for guiding said sound waves toward said workpiece, said channels having flow medium inlets and axes in alignment with said axes of said sound waves passing therethrough.

2. The ultrasound apparatus according to claim 1, wherein said at least two points of intersection are spaced at a distance and wherein said distance between said points of intersection of said axes of said sound waves is dimensioned so as to prevent disturbance generated by oppositely disposed testing heads for testing of longitudinal or slanting defects.

3. The ultrasound apparatus according to claim 1, wherein said points of intersection are located on a straight line parallel to a surface of said workpiece.

4. The ultrasound apparatus according to claim 2, further comprising a sound wave generator for generating said sound waves, said sound waves having a frequency, said sound wave generator having a size, said sound waves generated by said sound wave generator defining a sound wave funnel, said testing heads having a diameter, wherein said distance between said points of intersection is determined from the size of the sound wave generator, the frequency, and the sound wave funnel to be about $(n-1)$ times the diameter of said testing heads, wherein n represents the number of said points of intersection.

5. The ultrasound apparatus according to claim 1, wherein each of said channels has a circular cross section.

6. An ultrasound apparatus according to claim 1, wherein said axes of said channels intersect at at least one point at said flow medium outlet of said chamber.

7. The ultrasound apparatus according to claim 1, additionally comprising a ventilation duct in said testing head carrier, wherein said testing head carrier and said chamber are arranged relative to each other so that, in an area enclosing said testing heads and the flow medium inlets of said channels, a sealed slit opening is formed for guiding said flow medium therethrough said slit opening having first and second ends, said slit opening being connected at said first end to a space connecting said flow medium inlets of said channels, and at said second end to said ventilation duct.

8. The ultrasound apparatus according to claim 7, further comprising means for opening and closing said ventilation duct.

9. The ultrasound apparatus according to claim 1, further comprising: a bushing connected to said testing head carrier; and an exchangeable insert disposed within said bushing for guiding said flow medium.

10. The ultrasound apparatus according to claim 1, wherein said axes of said channels and said axes of said sound waves converge in at least one intersection located on a surface of said workpiece facing said flow medium outlet of said chamber.

11. The ultrasound apparatus according to claim 1, wherein said workpiece comprises a back wall, said sound waves converge in on said back wall of said workpiece, while said axes of said channels converge at a location spaced from said workpiece opposite the ultrasound apparatus.

* * * * *